United States Patent [19]

Molleyres

[11] Patent Number: 5,151,427
[45] Date of Patent: Sep. 29, 1992

[54] ANTHELMINITICS

[75] Inventor: Louis-Pierre Molleyres, Binningen, Switzerland

[73] Assignee: Ciba-Geigy Corporation, Ardsley, N.Y.

[21] Appl. No.: 619,272

[22] Filed: Nov. 28, 1990

[30] Foreign Application Priority Data

Dec. 1, 1989 [CH] Switzerland .......................... 4297/89

[51] Int. Cl.$^5$ ................. A61K 31/505; C07D 239/545
[52] U.S. Cl. .................................... 514/269; 514/241; 514/242; 514/243; 514/248; 514/249; 514/252; 514/259; 544/182; 544/183; 544/219; 544/238; 544/284; 544/296; 544/295; 544/319
[58] Field of Search ................. 544/319; 514/270, 269

[56] References Cited

U.S. PATENT DOCUMENTS

| | | | |
|---|---|---|---|
| 4,602,912 | 7/1986 | deSousa et al. | 8/127.5 |
| 4,636,508 | 1/1987 | Brewer et al. | 514/274 |
| 4,670,441 | 6/1987 | Kühne et al. | 514/270 |
| 4,748,178 | 5/1988 | Burkhardt et al. | 514/270 |
| 4,753,940 | 6/1988 | Sturm et al. | 514/252 |
| 4,879,276 | 11/1989 | Brewer et al. | 514/43 |

FOREIGN PATENT DOCUMENTS

| | | |
|---|---|---|
| 0167491 | 1/1986 | European Pat. Off. . |
| 0191474 | 8/1986 | European Pat. Off. . |
| 1464326 | 2/1977 | United Kingdom . |

OTHER PUBLICATIONS

Chem. Abstr. 103: 215, 248, Mikhavela et al., from Khimgs., (1985), 378-85.
Chem. Abstr: 113:6366, Brewer et al., Abstr. from South African Patent 88 03, 119 (Sep. 1989).
Chem Abstr. 112:139,048, Brewer et al., From BE 1,001,262 (Sep. 1989).
Chem Abstr. 112:198,414, Brewer et al., from FR 2,628,869 (Sep. 1989).
Chem Abstr. 112:118,846, Brewer et al., from BE 1,001,263 (Sep. 1989).
Chem Abstr. 111:225,323, Warrell et al., from WO 8810,114 (Jun. 1987).
G. W. Benz et al., Amer. J. Vet Res., 38, pp. 1425-1426 (1976).
V. J. Theodorides et al., Amer. J. Vet. Res., 37, 1515-1516 (1976).
R. A. Knight et al., Amer. J. Vet. Res., 38, 807-808 (1976).
H. Herlick, Amer. J. Vet. Res., 38 pp. 1247-1248 (1977).

*Primary Examiner*—Mukund J. Shah
*Assistant Examiner*—Matthew V. Grumbling
*Attorney, Agent, or Firm*—Marla J. Mathias; McC. Edward Roberts

[57] ABSTRACT

Novel anthelmintics are described which, as active ingredient, contain a compound of the formula I

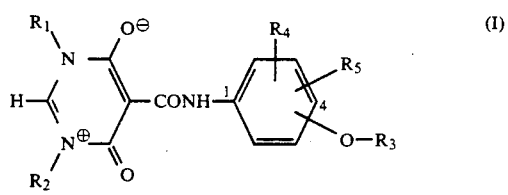

or in its hydrogenated form the formula (Ia)

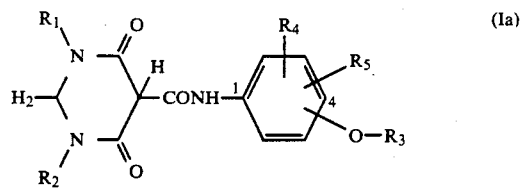

in which $R_1$ and $R_2$ independently of one another are $C_1$-$C_6$alkyl, allyl, $C_3$-$C_6$cycloalkyl, benzyl or phenyl; $R_3$ is an unsubstituted or substituted heteroaromatic 6-membered ring which contains 1, 2 or 3 nitrogen atoms or a benzo-fused, unsubstituted or substituted heteroaromatic 6-membered ring which contains 1 to 3 nitrogen atoms, and $R_4$ and $R_5$ independently of one another are hydrogen, $C_1$-$C_4$alkyl, $C_1$-$C_4$alkoxy or halogeno-$C_1$-$C_3$alkyl, including their tautomeric forms and physiologically tolerable salts. The preparation, formulation and use of these active ingredients are also described.

17 Claims, No Drawings

ANTHELMINITICS

The present invention relates to novel 1,3-disubstituted 6-ring heterocyclyloxyphenylcarbamoyl-4,6-pyrimidinedione derivatives of the formula I below and their hydrogenated analogs of the formula Ia below having anthelmintic activity; said substances for use in a process for controlling helminths; anthelmintic compositions which contain these substances as active ingredients; the preparation of the active ingredients and compositions; and the use of the active ingredients and/or compositions for controlling helminths, in particular nematodes, cestodes and trematodes in domestic animals and productive livestock of the mammalian class.

The compounds according to the invention have the formula I

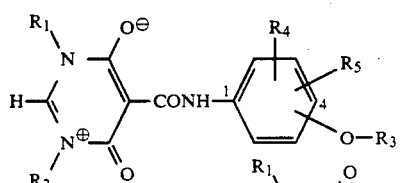

or in their hydrogenated form the formula (Ia)

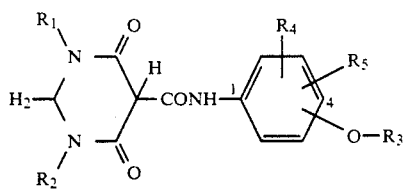

in which $R_1$ and $R_2$ independently of one another are $C_1-C_6$alkyl, allyl, $C_3-C_6$cycloalkyl, benzyl or phenyl; $R_3$ is an unsubstituted or substituted heteroaromatic 6-membered ring which contains 1,2 or 3 nitrogen atoms or a benzo-fused, unsubstituted or substituted heteroaromatic 6-membered ring which contains 1 to 3 nitrogen atoms, and $R_4$ and $R_5$ independently of one another are hydrogen, $C_1-C_4$alkyl, $C_1-C_4$alkoxy or halogeno-$C_1-C_3$alkyl, including their tautomeric forms and physiologically tolerable salts.

In formula I, only one of the numerous possible betaine structures is represented, examples of other isoelectronic structural formulae are:

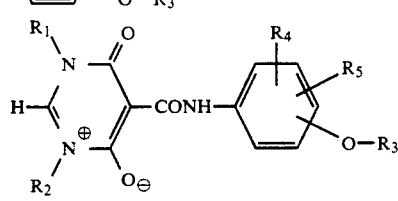 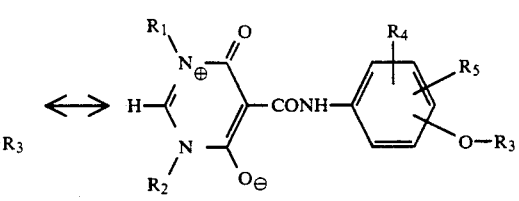

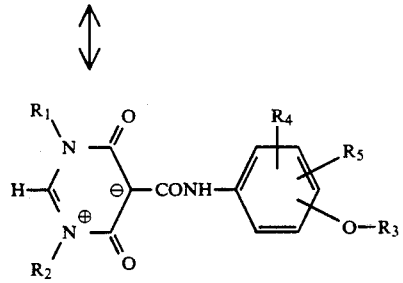 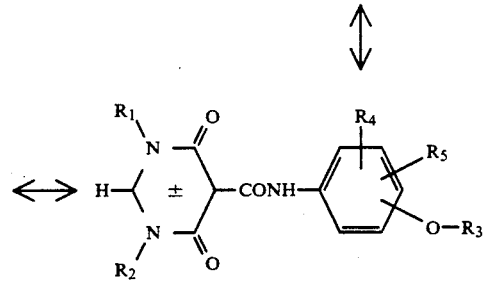

or briefly:

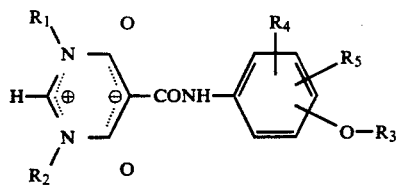

The compounds of the formula Ia can be present, for example, in the following tautomeric forms:

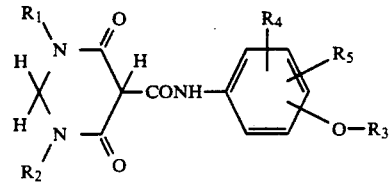 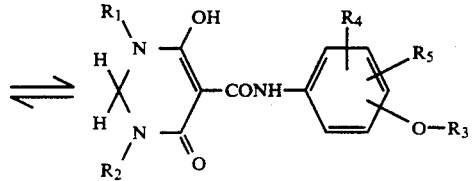

The compounds of the formulae I and Ia are constituents of the present invention in all forms.

In the context of the present invention, depending on the number of carbon atoms indicated, the term alkyl itself or as a constituent of another substituent is to be understood as meaning the following straight-chain and branched groups, for example: methyl, ethyl, n-propyl, iso-propyl, n-butyl, sec-butyl, tert-butyl, isobutyl, etc. Haloalkyl itself or as a constituent of haloalkoxy is a mono- to perhalogenated alkyl substituent, such as, for example, $CH_2Cl$, $CHCl_2$, $CCl_3$, $CH_2F$, $CHF_2$, $CF_3$, $CH_2Br$, $CHBr_2$, $CBr_3$, $CH_2I$, $CI_3$, $CHClF$, $CHBrCl$, $CFBrCl$, $C_2F_5$, $CH_2CH_2Cl$, $CHClCH_3$, $C_2Cl_5$, $CHFCHCl_2$, etc., preferably $CF_3$. Halogen here and in the following should be understood as meaning fluorine, chlorine, bromine or iodine, preferably fluorine, chlorine or bromine, but primarily chlorine.

Depending on the number of carbon atoms indicated, cycloalkyl itself or as a component of a substituents is cyclopropyl, cyclobutyl, cyclopentyl, cyclohexyl, etc. Cyanoalkyl is an alkyl group in which a hydrogen atom is substituted by CN, preferably an alkyl group in which the CN group is on the terminal carbon atom.

The term physiologically tolerable salts of compounds of the formulae I and Ia is understood as weaning the alkali metal, ammonium or amine salts, sodium, potassium, ammonium or alkylamine salts, in particular triethylamine salts, being preferred. However, the addition salts of inorganic and organic acids which are formed by addition of an equivalent amount of a salt-forming acid to the basic molecule are also to be understood thereunder.

Examples of salt-forming acids are inorganic acids: hydrohalic acid such as hydrofluoric acid, hydrochloric acid, hydrobromic acid or hydriodic acid and sulfuric acid, phosphoric acid, phosphorous acid, nitric acid and organic acids, for example acetic acid, trifluoroacetic acid, trichloroacetic acid, propionic acid, glycolic acid, thiocyanic acid, lactic acid, succinic acid, citric acid, formic acid, benzenesulfonic acid, p-toluenesulfonic acid, methanesulfonic acid, salicylic acid, p-aminosalicylic acid, phthalic acid, 2-phenoxybenzoic acid or 2-acetoxybenzoic acid.

Possible substituents $R_3$ are, for example, unsubstituted or substituted representatives of the group comprising pyridine, pyrimidinyl, triazinyl, pyrazinyl, pyridazinyl, quinolyl, isoquinolyl, phthalazinyl, quinoxalyl, quinazolinyl, cinnolinyl and benzotriazinyl.

Substituents of the abovementioned rings and ring systems which may be mentioned are $C_1-C_4$alkyl, halogeno-$C_1-C_4$alkyl, alkoxyalkyl having a total of 2 to 4 carbon atoms, $C_1-C_4$alkoxy, halogen-$C_1-C_4$alkoxy, $C_1-C_4$alkylthio, halogeno-$C_1-C_4$alkylthio, $C_1-C_3$alkylamino, di-($C_1-C_3$alkyl)-amino, allyl, propargyl, halogen, nitro, cyano, $C_3-C_6$-cycloalkyl or phenyl.

A possible substituent $R_3$ is accordingly, for example, the following cyclic radicals:

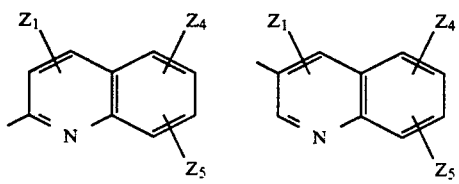

-continued

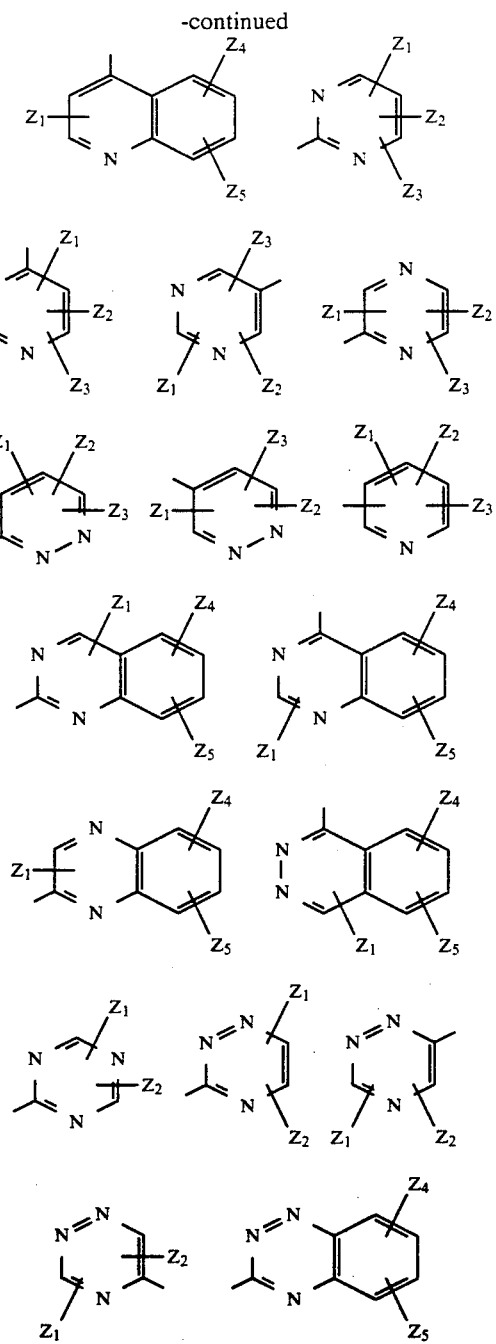

In the abovementioned radicals, $Z_1$, $Z_2$, $Z_3$, $Z_4$ and $Z_5$ are independently of one another hydrogen, $C_1-C_4$alkyl, halogen-$C_1-C_4$alkoxy, alkoxyalkyl having a total of 2 to 4 carbon atoms, $C_1-C_4$alkoxy, halogen-$C_1-C_4$alkoxy, $C_1-C_4$alkylthio, halogen-$C_1-C_4$alkylthio, $C_1-C_3$alkylamino, di-($C_1-C_3$alkyl)amino, allyl, propargyl, halogen, nitro, cyano, $C_3-C_6$cycloalkyl or phenyl, $Z_1$, $Z_2$ and $Z_3$ being on the heteroaromatic ring and $Z_4$ and $Z_5$ being on the fused homoaromatic ring, $Z_1$, $Z_2$, $Z_3$, $Z_4$ and $Z_5$ radicals particularly worthy of mention are halogen, preferably chlorine, and also trifluoromethyl and methylthio.

Examples of $C_1-C_4$alkoxy are methoxy, ethoxy, n-propoxy, isopropoxy, of $C_1-C_4$alkylthio methylthio and n-propylthio of halogen-$C_1-C_4$alkoxy chloromethoxy, fluoromethoxy, 2-chloroethoxy, 2,2-dichloroethoxy, 3-fluoro-n-propoxy and 2,2,2-trifluoroethoxy, and of halogen-$C_1$-$C_4$alkylthio fluoromethylthio, chloromethylthio, 1,2-dichloroethylthio and 2,2-difluoromethylthio.

In the context of the present invention, a di-($C_1$-$C_3$alkyl)amino radical is to be understood as meaning an amino group in which the two hydrogen atoms are replaced by two identical or different alkyl groups having 1 to 3 carbon atoms. The dimethylamino group is preferred.

The compounds of the formulae I and Ia are predominantly present at room temperature as stable solids which have a melting point of about 100° to about 300° C. They have very useful anthelmintic properties and can be employed for the curative and preventive control of a number of worm disorders in warm-blooded animals, in particular in domestic animals and productive livestock, primarily of the mammalian class.

Worthy of mention are compounds of the formula I in which $R_3$, $R_4$ and $R_5$ have the meanings given under formula I and $R_1$ and $R_2$ independently of one another are $C_1$-$C_6$alkyl, allyl, $C_3$-$C_6$cycloalkyl or phenyl.

Of particular interest are compounds of the formulae I and Ia in which $R_1$ and $R_2$ independently of one another are methyl, ethyl or allyl, and in particular those in which $R_1$ and $R_2$ independently of one another are methyl or phenyl, in particular methyl.

Of interest are also the representatives in the scope of the formulae I and Ia in which $R_3$ is an unsubstituted or substituted pyridine, pyrimidine or triazine, suitable substituents being methyl, halomethyl, in particular $CF_3$, halogen, in particular chlorine, methylthio and cyclopropyl.

One group of interest is compounds of the formulae I and Ia in which $R_1$ and $R_2$ independently of one another are $C_1$-$C_4$alkyl, allyl or cyclopropyl; $R_3$ is a pyridyl, pyrazinyl, pyridazinyl, triazinyl, pyrimidinyl, quinoxalinyl, quinolyl or quinazolinyl radical which is unsubstituted or mono- to trisubstituted by substituents of the group comprising $C_1$-$C_4$alkyl, preferably methyl, isopropyl and tert-butyl, methoxy, methylamino, dimethylamino, methylthio, trifluoromethyl, halogen, preferably chlorine, and phenyl, $R_4$ is hydrogen, $C_1$-$C_4$alkyl, preferably methyl or isopropyl, or methoxy, and $R_5$ is hydrogen or methyl.

Compounds of the formulae I and Ia are additionally to be particularly emphasized in which the structural element —$OR_3$ is on the phenyl ring in the meta- or in particular in the para-position, preferably in the para-position, to the carbamoyl radical.

A group which is particularly worthy of mention are compounds of the formula I in which $R_1$ and $R_2$ are methyl, $R_3$ is a pyridyl, pyrazinyl, pyrimidinyl, pyridazinyl, quinoxalinyl or quinolyl radical which is unsubstituted or mono- or disubstituted by substituents of the group comprising methyl, isopropyl, methoxy and chlorine, and $R_4$ and $R_5$ are hydrogen.

Of outstanding interest, however, are the following groups of compounds of the formulae I and Ia whose importance with respect to their activity increases from a) to f).

a) Compounds in which $R_1$ is $C_1$-$C_4$alkyl, allyl or $C_3$-$C_6$cycloalkyl, $R_2$ is $C_1$-$C_4$alkyl, $R_3$ is a pyridyl, pyrazinyl, pyrimidinyl, pyridazinyl, triazinyl, quinoxalinyl or quinolinyl radical which is unsubstituted or mono- to trisubstituted by substituents of the group comprising $C_1$-$C_4$alkyl, halogeno-$C_1$-$C_4$alkyl, $C_1$-$C_4$alkoxy, halogeno-$C_1$-$C_4$alkoxy, $C_1$-$C_4$alkylthio, $C_1$-$C_3$alkylamino, di-($C_1$-$C_3$alkyl)amino, allyl, halogen, $C_3$-$C_6$cycloalkyl and phenyl and which is bonded via a carbon atom, $R_4$ is hydrogen, $C_1$-$C_4$alkyl or $C_1$-$C_4$alkoxy, and $R_5$ is hydrogen;

b) compounds in which $R_1$ is $C_1$-$C_2$alkyl, allyl or cyclopropyl, $R_2$ is $C_1$-$C_2$alkyl, $R_3$ is a pyridyl, pyrazinyl, pyrimidinyl, pyridazinyl, triazinyl, quinoxalinyl or quinolinyl radical which is unsubstituted or mono- to trisubstituted by substituents from the group comprising $C_1$-$C_4$alkyl, halogeno-$C_1$-$C_4$alkyl, $C_1$-$C_4$alkoxy, $C_1$-$C_4$alkylthio, di-($C_1$-$C_3$alkyl)amino, halogen or phenyl and which is bonded via a carbon atom, $R_4$ is hydrogen, $C_1$-$C_4$alkyl or $C_1$-$C_4$alkoxy, and $R_5$ is hydrogen or $C_1$-$C_4$alkyl;

c) compounds in which $R_1$ is $C_1$-$C_2$alkyl, allyl or cyclopropyl, $R_2$ is methyl, $R_3$ is a pyridyl, pyrimidinyl, pyrazinyl or pyridazinyl radical which is unsubstituted or mono- to trisubstituted by substituents of the group comprising $C_1$-$C_4$alkyl, trifluoromethyl, methoxy, methylthio, chlorine or phenyl and which is bonded via a carbon atom, $R_4$ is hydrogen, $C_1$-$C_4$alkyl or $C_1$-$C_4$alkoxy and $R_5$ is hydrogen or $C_1$-$C_4$alkyl and the molecule moiety —$OR_3$ is in the meta- or para-position to the nitrogen atom of the carbamoyl group;

d) compounds in which $R_1$ is methyl or allyl, $R_2$ is methyl, $R_3$ is a pyridyl or pyrimidinyl ring which is unsubstituted or mono- or disubstituted by substituents of the group comprising $C_1$-$C_2$alkyl, halogeno-$C_1$-$C_2$alkyl, halogen or phenyl and which is bonded via a carbon atom, $R_4$ is hydrogen, $C_1$-$C_2$alkyl or $C_1$-$C_2$alkoxy, $R_5$ is hydrogen or methyl and the molecule moiety —$OR_3$ is in the meta- or para-position to the nitrogen atom of the carbamoyl group;

e) compounds in which $R_1$ is methyl, $R_2$ is methyl, $R_3$ is a pyridyl or pyrimidinyl ring which is mono- or disubstituted by substituents of the group comprising methyl, trifluoromethyl, chlorine and phenyl and which is bonded via a carbon atom, $R_4$ is hydrogen, methyl, isopropyl, methoxy or ethoxy, $R_5$ is hydrogen or methyl and the molecule moiety —$OR_3$ is in the meta- or para-position to the nitrogen atom of the carbamoyl group;

f) compounds in which $R_1$ is methyl, $R_2$ is methyl, $R_3$ is a pyridyl or pyrimidinyl ring which is monosubstituted by trifluoromethyl or in total disubstituted by trifluoromethyl and another substituent of the group comprising methyl, trifluoromethyl, chlorine and phenyl and which is bonded via a carbon atom, $R_4$ is hydrogen, methyl, isopropyl or methoxy, $R_5$ is hydrogen or methyl and the molecule moiety —$OR_3$ is in the para-position to the nitrogen atom of the carbamoyl group.

Particularly preferred individual representatives of the formula I are:
1,3-dimethyl-5-[4-(4-trifluoromethyl-6-chloropyridyl-2-oxy)-phenylcarbamoyl]-4(6)-oxo-6(4)-oxido-(1H,5H)-pyrimidinium betaine;
1,3-dimethyl-5-[4-(2-cyclopropyl-6-trifluoromethyl-pyrimidyl-4-oxy)-phenylcarbamoyl]-4(6)-oxo-6(4)-oxido-(1H,5H)-pyrimidinium betaine;
1,3-dimethyl-3-[3-(3-chloro-5-trifluoromethylpyridyl-2-oxy)-4-chlorophenylcarbamoyl]-4(6)-oxo-6(4)-oxido-(1H,5H)-pyrimidinium betaine;
1,3-dimethyl-5-[4-(4-trifluoromethylpyridyl-2-oxy)-phenylcarbamoyl]-4(6)-oxo-6(4)-oxido-(1H,5H)-pyrimidinium betaine;
1,3-dimethyl-5-[4-(3-chloro-5-trifluoromethylpyridyl-2-oxy)-phenylcarbamoyl]-4(6)-oxo-6(4)-oxido-(1H,5H)-pyrimidinium betaine.

Particularly preferred representatives of the formula Ia are:

1,3-dimethyl-5-[4-(4-trifluoromethyl-6-chloropyridyl-2-oxy)-phenylcarbamoyl]-4,6-(1H,3H,5H)-pyrimidinedione;

1,3-dimethyl-5-[4-(2-cyclopropyl-6-trifluoromethyl-pyrimidyl-4-oxy)-phenylcarbamoyl]-4,6-(1H,3H,5H)-pyrimidinedione;

1,3-dimethyl-3-[3-(3-chloro-5-trifluoromethylpyridyl-2-oxy)-4-chlorophenylcarbamoyl]-4,6-(1H,3H,5H)-pyrimidinedione;

1,3-dimethyl-5-[4-(4-trifluoromethylpyridyl-2-oxy)-phenylcarbamoyl]-4,6-(1H,3H,5H)-pyrimidinedione;

1,3-dimethyl-5-[4-(3-chloro-5-trifluoromethylpyridyl-2-oxy)-phenylcarbamoyl]-4,6-(1H,3H,5H)-pyrimidinedione.

The compounds of the formulae I and Ia are prepared according to the invention by desulfurizing a compound of the formula II

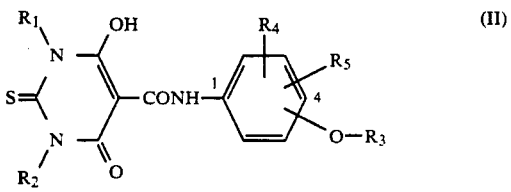

in which $R_1$, $R_2$ and $R_3$ have the meanings given under formulae I and Ia. The desulfurization can be carried out, for example, by hydrogenation, preferably by catalytic hydrogenation. In a preferred embodiment, the compound of the formula II is hydrogenated in a solvent or solvent mixture which is inert to the reaction at temperatures in the range from 20° to 180° C., preferably 60° to 120° C., in particular at reflux temperature, using trialkyltin hydride, trialkyltin halide, trialkylgermanium hydride, trialkylgermanium halide, alkylmercury hydride or alkylmercury halide, the reaction additionally being carried out in the presence of $NaBH_4$ when using a halide. Alkyl in this connection is preferably $C_1$–$C_6$alkyl, in particular $C_2$–$C_4$alkyl, and halide is in particular chloride or bromide. The chlorides are particularly suitable. Tris(trimethylsilyl)silane may be mentioned as a further suitable hydrogenating composition.

The hydrides and halides are employed in at least equimolar amount, relative to the starting compound of the formula II. $NaBH_4$ can also be added in an equimolar amount.

The reaction can additionally be carried out in the presence of a free radical initiator, in which case this can be added in catalytic amounts. Suitable free radical initiators are, for example, azoisobutyronitrile (AiBN), peroxides such as benzoyl peroxide, but also UV light or heat. Examples of suitable solvents which are inert to the reaction, alone or mixed with one another, are: aliphatic and aromatic hydrocarbons, such as, for example, pentane, hexane, petroleum ether, ligroin, benzene, toluene, xylenes, etc.; ethers and ether-like substances such as tetrahydrofuran, anisole, dioxane, etc.; halogenated hydrocarbons such as carbon tetrachloride, tetrachloroethylene, chlorobenzene, etc.

The compounds I and Ia are in general obtained together, it being possible to select the system by suitable choice of the solvent such that, for example, the poorly soluble betaines of the formula I precipitate and can be removed from the reaction mixture, for example, by filtration, while the more readily soluble compounds of the formula Ia can be obtained from the solution, for example, by concentrating or precipitating. However, a mixture of I and Ia can also be isolated and a separation can be carried out, for example, for instance by fractional crystallization or by column chromatography, on the basis of their differing solubility behaviour. However, under certain circumstances the skillful choice of the solvent also leads to pure products, i.e. either completely to I or to Ia. The compounds of the formula I can be converted by hydrogenation according to customary methods, for example with Raney nickel, $NaBH_4$, tributyltin hydride, etc., into the compounds of the formula Ia.

As already mentioned at the beginning, the compounds of the formula I and Ia can also be present as adducts with bases or acids.

While acid addition salts have already been described in depth at the beginning, the inorganic and organic bases which are suitable as adduct-forming compositions are still to be mentioned here. These are, for example, preferably tertiary amines such as trialkylamines (for example trimethylamine, triethylamine or tripropylamine), pyridine and pyridine bases (for example 4-dimethylaminopyridine or 4-pyrrolidylaminopyridine), picolines and lutidines and also oxides, hydroxides, carbonates and hydrogencarbonates of alkali metals and alkaline earth metals (for example CaO, BaO, NaOH, KOH, $Ca(OH)_2$, $KHCO_3$, $NaHCO_3$, $K_2CO_3$ or $Na_2CO_3$), and in addition acetates, for example $CH_3COONa$ or $CH_3COOK$. Moreover, suitable bases are also alkali metal alcoholates, for example sodium ethylate, sodium propylate, potassium tert-butylate or sodium methylate. The base is advantageously added in 10 to 100% of the equimolar amount relative to the reactants. In some cases it may be advantageous to carry out the reaction under a protective gas atmosphere. Suitable protective gases are, for example, nitrogen, helium or argon. The reaction of II with trialkyltin hydride, in particular in the presence of a free radical initiator, is particularly preferred.

The thiobarbiturates of the formula II are known, for example, from European Offenlegungsschriften EP 191,474, EP 135,155 and EP 167,491 or the corresponding British Published Specifications GB 2,174,388 B, GB 2,145,087 B and GB 2,163,423 B or can be prepared analogously to the representatives described therein.

The active ingredients of the formulae I and Ia according to the invention can be present in different tautomeric forms, namely in the keto or enol form or in a mixture of the keto and enol form. The present invention relates both to the individual tautomers and to their mixtures, but also to the salts of each of these forms and their preparation.

The preparation process described including all variants is a component of the present invention.

As is generally known, among the endoparasites occurring in warm-blooded animals, the helminths in particular cause great injury in the animals afflicted by them. Such injuries caused by helminthiases can take on to an economically crucial scale in chronic and in particular in epidemic occurrences of the worm diseases in livestock herds. They manifest themselves in the diseased animals, inter alia, in productivity losses, weakened resistance to other diseases and increased mortality. Particularly dangerous worm diseases are caused by helminths which are parasitic in the gastrointestinal tract and other organs and can occur, for example, in ruminants such as cattle, sheep and goats as well as horses, pigs, poultry, red deer, dogs and cats.

In the present description, the term helminths is in particular to be understood as meaning parasitic worms which include the Plathelminthes (cestodes, trematodes) and Nemathelminthes (nematodes and related), i.e. tapeworms, flukes and roundworms of the gastrointestinal tract and other organs (for example liver, lungs, kidneys, lymph vessels, blood etc.).

It is therefore an urgent aim to develop therapeutic compositions which are suitable for controlling helminths in all their stages of development and for prophylaxis against attack by these parasites.

Indeed, a number of substances having anthelmintic action are known which have been proposed for controlling the various helminth species. However, these are not completely satisfactory, either because at a tolerable dosage full utilization of their spectrum of action is not possible, or because in therapeutically active doses they show undesired side effects or properties. In this connection, the resistance against certain classes of substance which occurs increasingly today plays an ever more important role. The "albendazole" (British Pat. No. 1,464,326; Am. J. Vet. Res. 38, 1425-1426 (1977); Am. J. Vet. Res. 37, 1515-1516 (1976); Am. J. Vet. Res. 38, 807-808 (1977); Am. J. Vet. Res. 38, 1247-1248 (1977)) has only a limited anthelmintic spectrum of action in ruminants. Its action against benzimidazole-resistant nematodes and adult liver flukes is completely inadequate, the pathogenically important immature migratory forms of the latter, in particular, being unattacked at the doses which are tolerable for the host animal.

It has now surprisingly been found that the novel compounds of the formulae I and Ia have a wide spectrum of action against parasitic helminths such as nematodes, cestodes and trematodes in the animal organism, in particular in mammals, their action preferably being directed against nematodes (roundworms).

A particular feature of the compounds of the formulae I and Ia to be emphasized is their surprisingly high tolerability for warm-blooded animals, which makes them superior compared to the known thiobarbituric acid derivatives. Their practical handling in the treatment of worm-infested animals is extremely facilitated since they are also tolerated in higher doses by the medicated animals without symptoms.

The novel active compounds of the formulae I and Ia according to the invention are suitable, for example, for controlling parasitic nematodes of the orders (according to K. I. Skrajabin)
Rhabditida
Ascaridida
Spirurida
Trichocephalida
or for controlling cestodes of the orders (according to Wardle & McLeod)
Cyclophyllidae
Pseudophyllidae
or for controlling trematodes of the order
Digenea
in domestic animals and productive livestock such as cattle, sheep, goats, horses, pigs, red deer, cats, dogs and poultry. They can be administered to the animals both as an individual dose and repeatedly, the individual doses preferably being between 1 and 20 mg per kg of body weight, depending on the animal species. By means of a sustained administration. it is possible to obtain a better action in some cases or to manage with lower total doses.

The compositions according to the invention are prepared by bringing the active ingredients of the formula I or Ia into contact with liquid and/or solid formulation adjuncts by stepwise mixing and/or grinding in such a way that an optimum development of the anthelmintic activity of the formulation concurring with administration is achieved.

The formulation steps can be complemented by kneading, granulating (granules) and, if desired, pressing (pellets).

Formulation adjuncts used are, for example, solid excipients, solvents and, if desired, surface-active substances (surfactants).

To prepare the compositions according to the invention, the following formulation adjuncts are used: solid excipients such as, for example, kaolin, talc, bentonite, sodium chloride, calcium phosphate, carbohydrates, cellulose powder, cottonseed meal, polyethylene glycol ethers, if appropriate binders such as, for example, gelatine and soluble cellulose derivatives, if desired with the addition of surface-active substances such as ionic or non-ionic dispersing compositions; and in addition ground natural minerals such as calcite, montmorillonite or attapulgite. To improve the physical properties, highly disperse silicic acid or highly disperse absorbent polymers can also be added. Possible granulated adsorptive granules carriers are porous types, such as, for example, pumice, broken bricks, sepiolite or bentonite, and non-sorptive carrier materials are, for example, calcite or sand. Moreover, a multiplicity of pre-granulated materials of inorganic or organic nature such as, in particular, dolomite or comminuted plant material can be used.

Possible solvents are: aromatic hydrocarbons, preferably the fractions $C_8$ to $C_{12}$, for example xylene mixtures or substituted naphthalenes, phthalic acid esters such as dibutyl or dioctyl phthalate; aliphatic hydrocarbons, for example cyclohexane or paraffins, alcohols and glycols and their ethers and esters, for example ethanol, ethylene glycol, ethylene glycol monomethyl ether or ethylene glycol monoethyl ether, ketones, for example cyclohexanone, strongly polar solvents, for example N-methyl-2-pyrrolidone, dimethyl sulfoxide or dimethylformamide, and if appropriate epoxidized vegetable oils, for example epoxidized coconut oil or soya oil and water.

Depending on the nature of the active ingredient of the formula I or Ia to be formulated, possible surface-active compounds are non-ionic, cationic and/or anionic surfactants having good emulsifying, dispersing and wetting properties. Surfactants are also to be understood as meaning surfactant mixtures.

Suitable anionic surfactants can be both so-called water-soluble soaps and water-soluble synthetic surface-active compounds.

Soaps which may be mentioned are the alkali metal, alkaline earth metal or substituted or unsubstituted ammonium salts of higher fatty acids ($C_{10}$-$C_{22}$), for example the Na or K salts of oleic or stearic acid, or of natural fatty acid mixtures which can be obtained, for example, from coconut or tallow oil. In addition, the fatty acid methyltaurine salts may also be mentioned.

So-called synthetic surfactants are frequently used, in particular fatty sulfonates, fatty sulfates, sulfonated benzimidazole derivatives or alkylarylsulfonates.

The fatty sulfonates or sulfates are as a rule present as the alkali metal, alkaline earth metal or substituted or unsubstituted ammonium salts and have an alkyl radical having 8 to 22 C atoms, alkyl also including the alkyl moiety of acyl radicals, for example the Na or Ca salt of ligninsulfonic acid, of dodecylsulfuric acid ester or of a fatty alcohol sulfate mixture prepared from natural fatty acids. The salts of sulfuric acid esters and sulfonic acids of fatty alcohol-ethylene oxide adducts are also included here. The sulfonated benzimidazole derivatives preferably contain 2-sulfonic acid groups and a fatty acid radical having 8–22 C atoms. Alkylarylsulfonates are, for example, the Na, Ca or triethanolamine salts of dodecylbenzenesulfonic acid, dibutylnaphthalenesulfonic acid or of a naphthalenesulfonic acid-formaldehyde condensation product.

In addition, appropriate phosphates, for example salts of the phosphoric acid ester of a p-nonylphenol-(4–14)-ethylene oxide adduct or phospholipids are also suitable.

Suitable non-ionic surfactants are primarily polyglycol ether derivatives of aliphatic or cycloaliphatic alcohols, saturated or unsaturated fatty acids and alkylphenols which can contain 3 to 30 glycol ether groups and 8 to 20 carbon atoms in the aliphatic hydrocarbon radical and 6 to 18 carbon atoms in the alkyl radical of the alkylphenols.

Other suitable non-ionic surfactants are the water-soluble polyethylene oxide adducts of polypropylene glycol, ethylenediaminopolypropylene glycol and alkylpolypropylene glycol having 1 to 10 carbon atoms in the alkyl chain which contain 20 to 250 ethylene glycol ether groups and 10 to 100 propylene glycol ether groups. The compounds mentioned customarily contain 1 to 5 ethylene glycol units per propylene glycol unit.

Examples of non-ionic surfactants which may be mentioned are nonylphenolpolyethoxyethanols, castor oil polyglycol ethers, polypropylene-polyethylene oxide adducts, tributylphenoxypolyethoxyethanol, polyethylene glycol and octylphenoxypolyethoxyethanol.

In addition, fatty acid esters of polyoxyethylenesorbitan such as polyethylenesorbitan trioleate are also suitable.

The cationic surfactants are in particular quaternary ammonium salts which contain at least one alkyl radical having 8 to 22 C atoms as N substituents and lower, optionally halogenated alkyl, benzyl or lower hydroxyalkyl radicals as other substituents. The salts are preferably present as halides, methylsulfates or ethylsulfates, for example stearyltrimethylammonium chloride or benzyldi(2-chloroethyl)ethylammonium bromide.

The surfactants customary in formulation technology are described, inter alia, in the following publications:
"Mc Cutcheon's Detergents and Emulsifiers Annual",
  MC Publishing Corp., Ridgewood, N.J., 1980;
Sisley and Wood, "Encyclopedia of Surface Active
  compositions", Chemical Publishing Co., Inc. New
  York, 1980.

Suitable binders for tablets and boli are chemically modified, water- or alcohol-soluble, polymeric natural substances, such as starch, cellulose or protein derivatives (for example methyl cellulose, carboxymethyl cellulose, ethyl hydroxyethyl cellulose, proteins such as zein, gelatin and the like) and synthetic polymers, for example polyvinyl alcohol, polyvinylpyrrolidone etc. Fillers (for example starch, microcrystalline cellulose, sugar, lactose etc.), lubricants and disintegrants are additionally present in tablets.

If the anthelmintic compositions are present in the form of feed concentrates, carriers used are, for example, performance feeds, feed cereals or protein concentrates. Apart from the active ingredients, such feed concentrates or compositions may further contain additives, vitamins, antibiotics, chemotherapeutics, or other pesticides, principally bacteriostatics, fungistatics, coccidiostatics or, alternatively, hormone preparations, substances having anabolic action or encouraging growth, influencing the meat quality of animals for slaughter or substances useful to the organism in other ways. If the compositions or the active ingredients of the formula I contained therein are added directly to the feed or to the cattle drinking troughs, the finished feed or the finished drinks preferably contain the active compounds in a concentration of about 0.0005 to 0.02% by weight (5–200 ppm). The administration of the compositions according to the invention to the animals to be treated can be carried out perorally, parenterally or subcutaneously, the compositions being present in the form of solutions, emulsions, suspensions (drenches), powders, tablets, boli and capsules.

The anthelmintic compositions according to the invention as a rule contain 0.1 to 99% by weight, in particular 0.1 to 95% by weight, of active compound of the formula I, Ia or mixtures thereof, 99.9 to 1% by weight, in particular 99.8 to 5% by weight, of a solid or liquid additive, including 0 to 25% by weight, in particular 0.1 to 25% by weight, of a surfactant.

While concentrated compositions are preferred as commercial goods, the end consumer as a rule uses dilute compositions.

Such compositions may further contain other additives such as stabilizers, defoaming agents, viscosity regulators, binders, adhesives and other active ingredients to achieve specific effects.

Anthelmintic compositions of this type used by the end consumer are likewise a component of the present invention.

In each of the processes according to the invention for controlling pests or of the pesticides according to the invention, the active ingredients of the formulae I and Ia can be employed in all tautomeric forms, their mixtures or in the form of their salts.

The invention also includes a process for the prophylactic protection of animals against parasitic helminths, which comprises administering the active ingredients of the formulae I and Ia or the active ingredient formulations to the animals as an addition to the feed or to the drink or, alternatively, in solid or liquid form orally, by injection or parenterally.

The examples which follow are used to illustrate the invention without limiting it.

1. PREPARATION EXAMPLES

1.1. Preparation of 1,3-dimethyl-5-[4-(4-trifluoromethyl-6-chloro-pyridyl-2-oxy)-phenylcarbamoyl]-4(6)-oxo-6(4)-oxido-(1H,5H)-pyridinium betaine A solution of 8 g (16.5 mmol) of 1,3-dimethyl-5-[4-(4-trifluoromethyl-6-chloro-pyridyl-2-oxy)-phenylcarbamoyl]-2-thiobarbituric acid, 14.3 g (49.2 mmol) of tributyltin hydride and 207 mg (1.26 mmol) of azoisobutyronitrile in 350 ml of benzene is heated under reflux and under a nitrogen atmosphere for 45 minutes.

After cooling the reaction mixture, the product precipitated is filtered, washed several times with hexane and then suspended in benzene, and the solution is filtered hot. 1.7 g (23%) of the title substance are obtained. M.p. 295°–297° C.

$^1$H-NMR (300 MHz, DMSO d6, TMS): 11.06, s, NH; 9.38, s, H—C(3); 7.70, s, 1H; 7.69, d, J=9.5, 2H; 7.45, s, 1H; 7.15, d, J=9.5, 2H; 3.38, s, 2×CH$_3$.

1.2. Preparation of 1,3-dimethyl-5-[4-(4-trifluoromethyl-6-chloropyridyl-2-oxy)-phenylcarbamoyl]-4,6-(1H,3H,5H)-pyrimidined-ione The filtrate obtained according to Example 1.1. is concentrated and the product precipitated is filtered off and recrystallized using ethyl acetate. 4.1 g (55%) of the title substance are obtained. M.p. 174°–175° C.

$^1$H-NMR (300 MHz, CDCl$_3$, TMS): 18.22, s, OH; 11.87, s, NH; 7.55, d, J=9.5, 2H; 7.23, s, 1H; 7.12, d, J=9.5, 2H; 7.00, s, 1H; 4.49, s, H$_2$—C(3); 3.00, s, CH$_3$; 2.97, s, CH$_3$.

1.3. Preparation of 1,3-dimethyl-5-[4-(2-cyclopropyl-6-trifluoromethyl-pyrimidyl-4-oxy)-phenylcarbamoyl]-4(6)-oxo-6(4)-oxido-(1H,5H)-pyrimidinium betaine A solution of 9.9 g (0.01 mmol) of 1,3-dimethyl-5-[4-(2-cyclopropyl-6-trifluoromethylpyrimidyl-4-oxy)-phenylcarbamoyl]-2-thiobarbituric acid, 123 mg (0.75 mmol) of azoisobutyronitrile and 8 ml (0.03 mol) of tributyltin hydride are heated under reflux in 200 ml of benzene and under nitrogen for 1 hour. After cooling the reaction mixture, the product precipitated is washed with benzene, then several times with hexane and dried. 3.4 g (37%) of the title substance are obtained. M.p. 290°–291° C.

$^1$H-NMR (300 MHz, DMSO d6, TMS): 11.07, s, NH; 9.38, s, H—C(3); 7.70, d, J=7.5, 2H; 7.58, s, 1H; 7.18, d, J=7.5, 2H; 3.39, s, 2×CH$_3$; 2.16–2.07, m, 1H; 1.06–0.99, m, 2H; 0.90–0.83, m, 2H.

1.4. Preparation of 1,3-dimethyl-5-[4-(2-cyclopropyl-6-trifluoromethyl-pyrimidyl-4-oxy)-phenylcarbamoyl-4,6-(1H,3H,5H)-pyrimidinedione a) The filtrate from the above reaction according to 1.3. was concentrated and the residue was recrystallized from benzene. 4.8 g (52%) of the desired product are isolated.

$^1$H-NMR (300 MHz, CDCl$_3$, TMS): 18.24, s, OH; 11.90, s, NH; 7.55, d, J=9.5, 2H; 7.09, d, J=9.5, 2H; 6.88, s, 1H; 4.50, s, H$_2$—C(3); 3.01, s, CH$_3$; 2.96, s, CH$_3$; 2.24–2.12, m, 1H; 1.07–0.98, m, 4H.

b) A suspension of 461 mg (1 mmol) of 1,3-dimethyl-5-[4-(2-cyclopropyl-6-trifluoromethyl-pyrimidyl-4-oxy)-phenylcarbamoyl]-4(6)-oxo-6(4)-oxido-(1H,5H)-pyrimidinium betaine and 34 mg (1 mmol) of NaBH$_4$ in ethanol (10 ml) was stirred at room temperature under nitrogen for 2 hours. The reaction mixture cooled to 0° C. is acidified with 2N HCl, then neutralized with NaHCO$_3$ and extracted with ethyl acetate. The organic phase is washed with saturated NaHCO$_3$ solution and then with saturated NaCl solution, dried on MgSO$_4$ and concentrated. After crystallization in ethyl acetate, 337 mg (73%) of the title substance are obtained. M.p. 184°–187° C.

1.5. Preparation of 1,3-dimethyl-5-[3-(3-chloro-5-trifluoromethyl-pyridyl-2-oxy)-4-chlorophenylcarbamoyl]-4,6-(1H,3H,5)-pyrimidinedione A solution of 17.5 g (34 mmol) of 1,3-dimethyl-3-[3-(3-chloro-5-trifluoromethyl-pyridyl-2-oxy)-4-chlorophenylcarbamoyl]-2-thiobarbituric acid, 29.3 g (100 mmol) of tributyltin hydride and 490 mg (3 mmol) of azoisobutyronitrile is stirred under reflux in 750 ml of toluene for 7 hours, working under a nitrogen atmosphere. After cooling to room temperature, the mixture is concentrated and the product precipitated is filtered off, washed with hexane and dried in a high vacuum. 13.68 g (83%) of the title substance are obtained. M.p. 175°–185° C.

$^1$H-NMR (300 MHz, CDCl$_3$, TMS): 18.21, s, OH; 12.00, s, NH; 8.26, d, J<1, 1H; 8.00, d, J<1, 1H; 7.62, d J<1, 1H; 7.41, d, J=9, 1H; 7.30, d×d, J$_1$=9, J$_2$<1, 1H; 4.50, s, H$_2$—C(3); 3.01, s, CH$_3$; 2.95, s, CH$_3$.

The representatives of the formulae I and Ia mentioned in the following tables can be prepared analogously to the procedures described.

TABLE 1

Pyrimidinium betaine derivatives of the formula

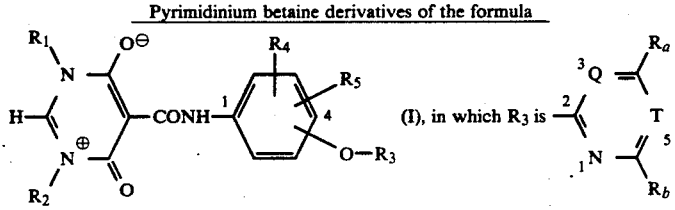

(I), in which R$_3$ is

| Compound No. | R$_1$ | R$_2$ | R$_4$ | R$_5$ | Position of OR$_3$ | Q | T | R$_a$ | R$_b$ | m.p. [°C.] |
|---|---|---|---|---|---|---|---|---|---|---|
| 1.1 | CH$_3$ | CH$_3$ | H | H | 4 | C—Cl | C—CF$_3$ | H | H | 270–275° |
| 1.2 | CH$_3$ | CH$_3$ | H | H | 4 | CH | N | CF$_3$ | Cyclopropyl | 290–291° |
| 1.3 | CH$_3$ | CH$_3$ | H | H | 4 | CH | CH | CF$_3$ | H | 295–297° |
| 1.4 | CH$_3$ | CH$_3$ | H | H | 4 | CH | CH | CF$_3$ | Cl | 293–295° |
| 1.5 | CH$_3$ | CH$_3$ | H | 4-Cl | 3 | C—Cl | C—CF$_3$ | H | H | 304–305° |
| 1.6 | CH$_3$ | CH$_3$ | H | H | 4 | CH | N | Cl | H | |
| 1.7 | CH$_3$ | CH$_3$ | H | H | 4 | N | CH | CH$_3$ | CH$_3$ | |
| 1.8 | CH$_3$ | CH$_3$ | H | H | 4 | CH | N | CH$_3$ | SCH$_3$ | |
| 1.9 | CH$_3$ | CH$_3$ | H | H | 4 | CH | N | Cl | C(CH$_3$)$_2$CH$_2$Cl | |
| 1.10 | CH$_3$ | CH$_3$ | H | H | 4 | CH | N | Cl | CH$_3$ | |
| 1.11 | CH$_3$ | CH$_3$ | H | H | 4 | CH | N | H | SCH$_3$ | |

TABLE 1-continued

Pyrimidinium betaine derivatives of the formula (I), in which $R_3$ is shown

| Compound No. | $R_1$ | $R_2$ | $R_4$ | $R_5$ | Position of $OR_3$ | Q | T | $R_a$ | $R_b$ | m.p. [°C.] |
|---|---|---|---|---|---|---|---|---|---|---|
| 1.12 | $CH_3$ | $CH_3$ | H | H | 4 | $C-CF_3$ | N | H | Cl | |
| 1.13 | $CH_3$ | $CH_3$ | H | H | 4 | N | $C-CH_3$ | H | H | |
| 1.14 | $CH_3$ | $CH_3$ | H | H | 4 | N | $C-CF_3$ | H | H | |
| 1.15 | $CH_3$ | $C_2H_5$ | H | H | 4 | CH | N | $CF_3$ | Cyclopropyl | 286–288° |
| 1.16 | $CH_3$ | $CH_2CH=CH_2$ | H | H | 4 | CH | N | $CF_3$ | Cyclopropyl | |
| 1.17 | $CH_3$ | $CH_3$ | 2-$OCH_3$ | H | 4 | CH | N | $CF_3$ | H | |
| 1.18 | $CH_3$ | $CH_3$ | 2-$CH_3$ | H | 4 | CH | N | H | $CF_3$ | |
| 1.19 | $CH_3$ | $CH_3$ | 3-Cl | H | 4 | C-Cl | $C-CF_3$ | H | H | |
| 1.20 | $CH_3$ | $CH_3$ | H | H | 4 | CH | $C-CF_3$ | H | H | 265–266° |
| 1.21 | $CH_3$ | $CH_3$ | 2-isopropyl | H | 4 | CH | $C-CF_3$ | H | H | |
| 1.22 | $CH_3$ | $CH_3$ | H | H | 3 | CH | $C-NO_2$ | H | H | |
| 1.23 | $CH_3$ | $CH_3$ | H | H | 4 | C-Cl | C-Cl | H | H | 320–322° |
| 1.24 | $CH_3$ | $C_2H_5$ | H | H | 4 | CH | CH | $CF_3$ | H | 278–280° |
| 1.25 | $CH_3$ | $C_2H_5$ | H | H | 4 | C-Cl | $C-CF_3$ | H | H | |
| 1.26 | $CH_3$ | $C_2H_5$ | H | H | 4 | CH | CH | $CF_3$ | Cl | |
| 1.27 | $CH_3$ | $CH_2CH=CH_2$ | H | H | 4 | CH | CH | $CF_3$ | H | 260–262° |
| 1.28 | $CH_3$ | $CH_2CH=CH_2$ | H | H | 4 | CH | CH | $CF_3$ | Cl | |
| 1.29 | $CH_3$ | $CH_2CH=CH_2$ | H | H | 4 | C-Cl | $C-CF_3$ | H | H | |
| 1.30 | $CH_3$ | $CH_3$ | 2-$CH_3$ | H | 4 | CH | CH | $CF_3$ | H | |
| 1.31 | $CH_3$ | $CH_3$ | 3-$OCH_3$ | H | 4 | CH | CH | $CF_3$ | H | |
| 1.32 | $C_2H_5$ | $C_2H_5$ | 2-Cl | 6-Cl | 4 | CH | CH | $CF_3$ | H | |
| 1.33 | $CH_3$ | $CH_3$ | 2-$CH_3$ | H | 4 | C-Cl | $C-CF_3$ | H | H | 261–263° |
| 1.34 | $CH_3$ | $CH_3$ | 2-F | H | 4 | C-Cl | $C-CF_3$ | H | H | 265–267° |
| 1.35 | $CH_3$ | $CH_3$ | 2-$CF_3$ | H | 4 | C-Cl | C-Cl | H | H | 295–296° |
| 1.36 | $CH_3$ | $CH_3$ | 2-$C_2H_5$ | 2-$C_2H_5$ | 4 | N | CH | H | H | |
| 1.37 | $CH_3$ | $CH_3$ | 2-$CH_3$ | 6-$CH_3$ | 4 | C-Cl | $C-CF_3$ | H | H | |
| 1.38 | $CH_3$ | $CH_3$ | 3-Cl | H | 4 | N | N | $OCH_3$ | $OCH_3$ | 281–283° |
| 1.39 | $CH_3$ | $CH_3$ | H | H | 4 | N | N | $OCH_3$ | $OCH_3$ | 280–282° |
| 1.40 | $CH_3$ | $CH_3$ | 2-$CH_3$ | 6-$CH_3$ | 4 | CH | $C-CF_3$ | H | H | |
| 1.41 | $CH_3$ | $CH_3$ | 2-$CH_3$ | 6-$CH_3$ | 4 | N | CH | H | H | 308–310° |
| 1.42 | $CH_3$ | $CH_3$ | H | H | 4 | $C-CH_3$ | C-Cl | $CH_3$ | N | |
| 1.43 | $CH_3$ | $CH_3$ | 2-$CH_3$ | 6-$CH_3$ | 4 | CH | C-Cl | H | N | |
| 1.44 | $CH_3$ | $CH_3$ | 2-Cl | 6-Cl | 4 | CH | CH | H | H | |
| 1.45 | $CH_3$ | $CH_3$ | 2-$CH_3$ | 6-$CH_3$ | 4 | C-Cl | C-Cl | H | H | |
| 1.46 | $CH_3$ | $CH_3$ | 3-Cl | 5-Cl | 4 | C-Cl | $C-CF_3$ | H | H | |
| 1.47 | $CH_3$ | $CH_3$ | H | H | 4 | C-Cl | $C-C_2Cl_5$ | H | H | |
| 1.48 | $CH_3$ | $CH_3$ | 3-Cl | H | 4 | C-Cl | $CCF_2CF_2Cl$ | H | H | |
| 1.49 | $CH_3$ | $CH_3$ | H | H | 4 | C-Cl | $CCF_2CF_2Cl$ | H | H | |
| 1.50 | $CH_3$ | $CH_3$ | 3-Cl | H | 4 | CH | CH | $CF_3$ | Cl | |
| 1.51 | $CH_3$ | $CH_3$ | 3-F | H | 4 | C-F | C-Cl | H | H | |
| 1.52 | $CH_3$ | $CH_3$ | 2-$C_3H_7i$ | 6-$C_3H_7i$ | 4 | C-Cl | $CF_3$ | H | H | |

TABLE 2

Pyrimidine dione derivatives of the formula (Ia), in which $R_3$ is shown

| Compound No. | $R_1$ | $R_2$ | $R_4$ | $R_5$ | Position of $OR_3$ | Q | T | $R_a$ | $R_b$ | m.p. [°C.] |
|---|---|---|---|---|---|---|---|---|---|---|
| 2.1 | $CH_3$ | $CH_3$ | H | H | 4 | C-Cl | $C-CF_3$ | H | H | 144–145° |
| 2.2 | $CH_3$ | $CH_3$ | H | H | 4 | CH | N | $CF_3$ | Cyclopropyl | 184–187° |
| 2.3 | $CH_3$ | $CH_3$ | H | H | 4 | CH | CH | $CF_3$ | H | 194–196° |
| 2.4 | $CH_3$ | $CH_3$ | H | H | 4 | CH | CH | $CF_3$ | Cl | 174–175° |
| 2.5 | $CH_3$ | $CH_3$ | H | 4-Cl | 3 | C-Cl | $C-CF_3$ | H | H | 199–200° |
| 2.6 | $CH_3$ | $CH_3$ | H | H | 4 | CH | N | Cl | H | |
| 2.7 | $CH_3$ | $CH_3$ | H | H | 4 | N | CH | $CH_3$ | $CH_3$ | |
| 2.8 | $CH_3$ | $CH_3$ | H | H | 4 | CH | N | $CH_3$ | $SCH_3$ | |
| 2.9 | $CH_3$ | $CH_3$ | H | H | 4 | CH | N | Cl | $C(CH_3)_2CH_2Cl$ | |
| 2.10 | $CH_3$ | $CH_3$ | H | H | 4 | CH | N | Cl | $CH_3$ | |

TABLE 2-continued

Pyrimidine dione derivatives of the formula (Ia), in which $R_3$ is shown

| Compound No. | $R_1$ | $R_2$ | $R_4$ | $R_5$ | Position of $OR_3$ | Q | T | $R_a$ | $R_b$ | m.p. [°C.] |
|---|---|---|---|---|---|---|---|---|---|---|
| 2.11 | $CH_3$ | $CH_3$ | H | H | 4 | CH | N | H | $SCH_3$ | – |
| 2.12 | $CH_3$ | $CH_3$ | H | H | 4 | C—$CF_3$ | N | H | Cl | |
| 2.13 | $CH_3$ | $CH_3$ | H | H | 4 | N | C—$CH_3$ | H | H | |
| 2.14 | $CH_3$ | $CH_3$ | H | H | 4 | N | C—$CF_3$ | H | H | |
| 2.15 | $CH_3$ | $C_2H_5$ | H | H | 4 | CH | N | $CH_3$ | Cyclopropyl | 128–129° |
| 2.16 | $CH_3$ | $CH_2CH=CH_2$ | H | H | 4 | CH | N | $CF_3$ | Cyclopropyl | 165–166° |
| 2.17 | $CH_3$ | $CH_3$ | 2-$OCH_3$ | H | 4 | CH | N | $CF_3$ | H | |
| 2.18 | $CH_3$ | $CH_3$ | 2-$CH_3$ | H | 4 | CH | N | H | $CF_3$ | |
| 2.19 | $CH_3$ | $CH_3$ | 3-Cl | H | 4 | C—Cl | C—$CF_3$ | H | H | |
| 2.20 | $CH_3$ | $CH_3$ | H | H | 4 | CH | C—$CF_3$ | H | H | 133–135° |
| 2.21 | $CH_3$ | $CH_3$ | 2-isopropyl | H | 4 | CH | C—$CF_3$ | H | H | |
| 2.22 | $CH_3$ | $CH_3$ | H | H | 3 | CH | C—$NO_2$ | H | H | |
| 2.23 | $CH_3$ | $CH_3$ | H | H | 4 | C—Cl | C—Cl | H | H | 189–190° |
| 2.24 | $CH_3$ | $C_2H_5$ | H | H | 4 | CH | CH | $CF_3$ | H | 151–152° |
| 2.25 | $CH_3$ | $C_2H_5$ | H | H | 4 | C—Cl | C—$CF_3$ | H | H | 116–117° |
| 2.26 | $CH_3$ | $C_2H_5$ | H | H | 4 | CH | CH | $CF_3$ | Cl | 139–141° |
| 2.27 | $CH_3$ | $CH_2CH=CH_2$ | H | H | 4 | CH | CH | $CF_3$ | H | 111–113° |
| 2.28 | $CH_3$ | $CH_2CH=CH_2$ | H | H | 4 | CH | CH | $CF_3$ | Cl | 154–156° |
| 2.29 | $CH_3$ | $CH_2CH=CH_2$ | H | H | 4 | C—Cl | C—$CF_3$ | H | H | 135–137° |
| 2.30 | $CH_3$ | $CH_3$ | 2-$CH_3$ | H | 4 | CH | CH | $CF_3$ | H | |
| 2.31 | $CH_3$ | $CH_3$ | 3-$OCH_3$ | H | 4 | CH | CH | $CF_3$ | H | |
| 2.32 | $C_2H_5$ | $C_2H_5$ | 2-Cl | 6-Cl | 4 | CH | CH | $CF_3$ | H | |
| 2.33 | $CH_3$ | $CH_3$ | 2-$CH_3$ | H | 4 | C—Cl | C—$CF_3$ | H | H | 178–180° |
| 2.34 | $CH_3$ | $CH_3$ | 2-F | H | 4 | C—Cl | C—$CF_3$ | H | H | 152–154° |
| 2.35 | $CH_3$ | $CH_3$ | 2-$CF_3$ | H | 4 | C—Cl | C—Cl | H | H | 148–150° |
| 2.36 | $CH_3$ | $CH_3$ | 2-$C_2H_5$ | 6-$C_2H_5$ | 4 | N | CH | H | H | 112–114° |
| 2.37 | $CH_3$ | $CH_3$ | 2-$CH_3$ | 6-$CH_3$ | 4 | C—Cl | $CF_3$ | H | H | 160–162° |
| 2.38 | $CH_3$ | $CH_3$ | 3-Cl | H | 4 | N | N | $OCH_3$ | $OCH_3$ | 222–223° |
| 2.39 | $CH_3$ | $CH_3$ | H | H | 4 | N | N | $OCH_3$ | $OCH_3$ | 196–197° |
| 2.40 | $CH_3$ | $CH_3$ | 2-$CH_3$ | 6-$CH_3$ | 4 | CH | C—$CF_3$ | H | H | 168–169° |
| 2.41 | $CH_3$ | $CH_3$ | 2-$CH_3$ | 6-$CH_3$ | 4 | N | CH | H | H | 183–185° |
| 2.42 | $CH_3$ | $CH_3$ | H | H | 4 | C—$CH_3$ | C—Cl | $CH_3$ | N | |
| 2.43 | $CH_3$ | $CH_3$ | 2-$CH_3$ | 6-$CH_3$ | 4 | CH | C—Cl | H | N | |
| 2.44 | $CH_3$ | $CH_3$ | 2-Cl | 6-Cl | 4 | CH | CH | H | H | |
| 2.45 | $CH_3$ | $CH_3$ | 2-$CH_3$ | 6-$CH_3$ | 4 | C—Cl | C—Cl | H | H | |
| 2.46 | $CH_3$ | $CH_3$ | 3-Cl | 5-Cl | 4 | C—Cl | C—$CF_3$ | H | H | |
| 2.47 | $CH_3$ | $CH_3$ | H | H | 4 | C—Cl | C—$C_2Cl_5$ | H | H | |
| 2.48 | $CH_3$ | $CH_3$ | 3-Cl | H | 4 | C—Cl | $CCF_2CF_2Cl$ | H | H | |
| 2.49 | $CH_3$ | $CH_3$ | H | H | 4 | C—Cl | $CCF_2CF_2Cl$ | H | H | |
| 2.50 | $CH_3$ | $CH_3$ | 3-Cl | H | 4 | CH | CH | $CF_3$ | Cl | |
| 2.51 | $CH_3$ | $CH_3$ | 3-F | H | 4 | C—F | C—Cl | H | H | |
| 2.52 | $CH_3$ | $CH_3$ | 2-$C_3H_7i$ | 6-$C_3H_7i$ | 4 | C—Cl | $CF_3$ | H | H | |

TABLE 3

Pyrimidinium betaine derivatives of the formula (I) in which $R_3$ is the following

| Compound No. | $R_1$ | $R_2$ | $R_4$ | $R_5$ | Position of $OR_3$ | E | $Z_a$ | $Z_b$ | $Z_c$ | $Z_d$ | m.p. [°C.] |
|---|---|---|---|---|---|---|---|---|---|---|---|
| 3.1 | $CH_3$ | $CH_3$ | H | H | 4 | N | H | Cl | H | H | |
| 3.2 | $CH_3$ | $CH_3$ | H | H | 4 | N | Cl | H | H | H | |
| 3.3 | $CH_3$ | $CH_3$ | H | H | 4 | N | H | F | H | H | |
| 3.4 | $CH_3$ | $CH_3$ | H | H | 4 | CH | H | H | H | H | |
| 3.5 | $CH_3$ | $CH_3$ | H | 4-Cl | 3 | N | H | H | H | H | |
| 3.6 | $CH_3$ | $CH_3$ | H | H | 4 | CH | H | Cl | H | H | |
| 3.7 | $CH_3$ | $CH_3$ | H | H | 4 | CH | H | H | Cl | Cl | |
| 3.8 | $CH_3$ | $CH_3$ | H | H | 4 | CH | H | H | H | Cl | |
| 3.9 | $CH_3$ | $CH_3$ | H | H | 4 | CH | H | $CH_3$ | H | H | |

TABLE 3-continued
Pyrimidinium betaine derivatives of the formula (I) in which $R_3$ is the following

| Compound No. | $R_1$ | $R_2$ | $R_4$ | $R_5$ | Position of $OR_3$ | E | Za | Zb | Zc | Zd | m.p. [°C.] |
|---|---|---|---|---|---|---|---|---|---|---|---|
| 3.10 | $CH_3$ | $CH_3$ | H | H | 4 | N | H | H | Cl | $CH_3$ | |
| 3.11 | $CH_3$ | $CH_3$ | H | H | 4 | N | H | H | H | $SCH_3$ | |
| 3.12 | $CH_3$ | $CH_3$ | H | H | 4 | N | $CH_3$ | H | H | Cl | |
| 3.13 | $CH_3$ | $CH_3$ | H | H | 4 | CH | $CF_3$ | H | H | H | |
| 3.14 | $CH_3$ | $CH_3$ | H | H | 4 | CH | H | $CH_3$ | H | H | |
| 3.15 | $CH_3$ | $C_2H_5$ | H | H | 4 | N | H | H | $CF_3$ | Cyclopropyl | |
| 3.16 | $CH_3$ | $CH_2CH=CH_2$ | H | H | 4 | N | H | H | $CF_3$ | Cyclopropyl | |
| 3.17 | $CH_3$ | $CH_3$ | 2-$OCH_3$ | H | 4 | N | H | H | $CF_3$ | H | |

TABLE 4
Pyrimidinedione derivatives of the formula (Ia) in which $R_3$ is the following

| Compound No. | $R_1$ | $R_2$ | $R_4$ | $R_5$ | Position of $OR_3$ | E | Za | Zb | Zc | Zd | m.p. [°C.] |
|---|---|---|---|---|---|---|---|---|---|---|---|
| 4.1 | $CH_3$ | $CH_3$ | H | H | 4 | N | H | Cl | H | H | |
| 4.2 | $CH_3$ | $CH_3$ | H | H | 4 | N | Cl | H | H | H | |
| 4.3 | $CH_3$ | $CH_3$ | H | H | 4 | N | H | F | H | H | |
| 4.4 | $CH_3$ | $CH_3$ | H | H | 4 | CH | H | H | H | H | |
| 4.5 | $CH_3$ | $CH_3$ | H | 4-Cl | 3 | N | H | H | H | H | |
| 4.6 | $CH_3$ | $CH_3$ | H | H | 4 | CH | H | Cl | H | H | |
| 4.7 | $CH_3$ | $CH_3$ | H | H | 4 | CH | H | H | Cl | Cl | |
| 4.8 | $CH_3$ | $CH_3$ | H | H | 4 | CH | H | H | H | Cl | |
| 4.9 | $CH_3$ | $CH_3$ | H | H | 4 | CH | H | $CH_3$ | H | H | |
| 4.10 | $CH_3$ | $CH_3$ | H | H | 4 | N | H | H | Cl | $CH_3$ | |
| 4.11 | $CH_3$ | $CH_3$ | H | H | 4 | N | H | H | H | $SCH_3$ | |
| 4.12 | $CH_3$ | $CH_3$ | H | H | 4 | N | $CH_3$ | H | H | Cl | |
| 4.13 | $CH_3$ | $CH_3$ | H | H | 4 | CH | $CF_3$ | H | H | H | |
| 4.14 | $CH_3$ | $CH_3$ | H | H | 4 | CH | H | $CH_3$ | H | H | |
| 4.15 | $CH_3$ | $C_2H_5$ | H | H | 4 | N | H | H | $CF_3$ | Cyclopropyl | |
| 4.16 | $CH_3$ | $CH_2CH=CH_2$ | H | H | 4 | N | H | H | $CF_3$ | Cyclopropyl | |
| 4.17 | $CH_3$ | $CH_3$ | 2-$OCH_3$ | H | 4 | N | H | H | $CF_3$ | H | |

2. FORMULATION EXAMPLES (%=PER CENT BY WEIGHT)

2.1. Emulsion concentrates

| | a) | b) | c) |
|---|---|---|---|
| Active ingredient from Tables 1 to 4 | 25% | 40% | 50% |
| Ca dodecylbenzenesulfonate | 5% | 8% | 6% |
| Castor oil polyethylene glycol ether (36 mol of ethylene oxide) | 5% | — | — |
| Tributylphenol polyethylene glycol ether (30 mol of ethylene oxide) | — | 12% | 4% |
| Cyclohexanone | — | 15% | 20% |
| Xylene mixture | 65% | 25% | 20% |

Emulsions of any desired concentration can be prepared from these concentrates by dilution with water.

2.2. Emulsion concentrates

| | a) | b) | c) |
|---|---|---|---|
| Active ingredient from Tables 1 to 4 | 10% | 8% | 60% |
| Octylphenol polyethylene glycol ether (4–5 mol of ethylene oxide) | 3% | 3% | 2% |
| Ca dodecylbenzenesulfonate | 3% | 4% | 4% |
| Castor oil polyethylene glycol ether (35 mol of ethylene oxide) | 4% | 5% | 4% |
| Cyclohexanone | 30% | 40% | 15% |
| Xylene mixture | 50% | 40% | 15% |

Emulsions of any desired concentration can be prepared from these concentrates by dilution with water.

2.3. Suspension concentrate

| | |
|---|---|
| Active ingredient from Tables 1 to 4 | 40% |
| Ethylene glycol | 10% |

-continued

|  |  |
|---|---|
| Nonylphenol polyethylene glycol ether (15 mol of ethylene oxide) | 6% |
| Na ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active ingredient is mixed intimately with the additives. A suspension concentrate is thus obtained from which suspensions of any desired concentration can be prepared by dilution with water.

2.4. Powder mixtures dispersible in water

|  | a) | b) | c) |
|---|---|---|---|
| Active ingredient from Tables 1 to 4 | 25% | 50% | 75% |
| Na ligninsulfonate | 5% | 5% | — |
| Oleic acid | 3% | — | 5% |
| Na diisobutylnaphthalenesulfonate | — | 6% | 10% |
| Octylphenolpolyethylene glycol ether (7-8 mol of ethylene oxide) | — | 2% | — |
| Highly disperse silicic acid | 5% | 10% | 10% |
| Kaolin | 62% | 27% | — |

The active ingredient is well mixed with the additives and well ground in a suitable mill. Wettable powders are obtained which can be diluted with water to give suspensions of any desired concentration.

2.5. Dusts

|  | a) | b) |
|---|---|---|
| Active ingredient from Tables 1 to 4 | 2% | 5% |
| Highly disperse silicic acid | 1% | 5% |
| Talc | 95% | — |
| Kaolin | — | 90% |

Ready-to-use dusts are obtained by intimately mixing the carriers with the active ingredient and grinding the mixture.

2.6. Granules

|  | a) | b) |
|---|---|---|
| Active ingredient from Tables 1 to 4 | 5% | 10% |
| Kaolin | 94% | — |
| Highly disperse silicic acid | 1% | — |
| Attapulgite | — | 90% |

The active ingredient is dissolved in methylene chloride and sprayed onto the carrier, and the solvent is then evaporated in vacuo. Such granules can be admixed with the feed.

2.7. Granules

|  |  |
|---|---|
| Active ingredient from Tables 1 to 4 | 10% |
| Na ligninsulfonate | 2% |
| Carboxymethylcellulose | 1% |
| Kaolin | 87% |

The active ingredient is mixed with the additives, ground and moistened with water. This mixture is extruded and then dried in a stream of air.

2.8. Granules

|  |  |
|---|---|
| Active ingredient from Tables 1 to 4 | 3% |
| Polyethylene glycol (MW 200) | 3% |
| Kaolin | 94% |

(MW = molecular weight)

The finely ground active ingredient is uniformly applied in a mixer to the kaolin moistened with polyethylene glycol. Dust-free coated granules are obtained in this manner.

2.9. Tablets and/or boli

| | | |
|---|---|---|
| I | Active ingredient from Tables 1 to 4 | 33.00% |
|  | Methylcelluose | 0.80% |
|  | Silicic acid, highly disperse | 0.80% |
|  | Cornflour | 8.40% |
| II | Lactose, cryst. | 22.50% |
|  | Cornflour | 17.00% |
|  | Microcryst. cellulose | 16.50% |
|  | Magnesium stearate | 1.00% |
| I | Methylcellulose is stirred into water. After the material has swollen, silicic acid is stirred in and the mixture is homogeneously suspended. Active ingredient and cornflour are mixed. The aqueous suspension is incorporated into this mixture and kneaded to give a dough. The material thus obtained is granulated through a 12M sieve and dried. | |
| II | All 4 adjuncts are well mixed. | |
| III | The premixes obtained according to I and II are mixed and compressed to give tablets or boli. | |

2.4. Injectables

A. Oily vehicle (slow release)

|  |  |
|---|---|
| An active ingredient from Tables 1 to 4 | 0.1–1.0 g |
| Groundnut oil | to 100 ml |
| An active ingredient from Tables 1 to 4 | 0.1–1.0 g |
| Sesame oil | to 100 ml |

Preparation: The active ingredient is dissolved in a part of the oil with stirring and, if necessary, gentle warming, made up to the intended volume after cooling and sterile filtered through a suitable 0.22 μm membrane filter.

B. Water-miscible solvent (medium release rate)

|  |  |
|---|---|
| An active ingredient from Tables 1 to 4 | 0.1–1.0 g |
| 4-Hydroxymethyl-1,3-dioxolane (glycerol formal) | 40 g |
| 1,2-Propanediol | to 100 ml |
| An active ingredient from Table 1 or 2 | 0.1–1.0 g |
| Glycerol dimethyl ketal | 40 g |
| 1,2-Propanediol | to 100 ml |

Preparation: The active ingredient is dissolved in a part of the solvent with stirring, made up to the intended volume and sterile filtered through a suitable 0.22 μm membrane filter.

C. Aqueous solubilizate (rapid release)

|  |  |
|---|---|
| An active ingredient from Tables 1 to 4 | 0.1–1.0 g |
| Polyethoxylated castor oil (40 ethylene oxide units) | 10 g |
| 1,2-Propanediol | 20 g |
| Benzyl alcohol | 1 g |

| -continued | |
|---|---|
| Waer for injection | to 100 ml |
| An active ingredient from Tables 1 to 4 | 0.1-1.0 g |
| Polyethoxylated sorbitan monooleate (20 ethylene oxide units) | 8 g |
| 4-Hydroxymethyl-1,3-dioxolane (glycerol formal) | 20 g |
| Benzyl alcohol | 1 g |
| Water for injection | to 100 ml |

Preparation: The active ingredient is dissolved in the solvents and the surfactant and made up to the intended volume with water. Sterile filtration through a suitable membrane filter having a pore diameter of 0.22 μm.

The aqueous systems may preferably also be employed for oral and/or intraruminal administration.

3. BIOLOGICAL EXAMPLES

The anthelmintic activity is demonstrated by the following tests:

3.1 Test on sheep infected with nematodes such as *Haemonchus contortus* and *Trichostrongylus colubriformis*

The active ingredient is administered in the form of a suspension using a stomach tube or by injection into the rumen to sheep which have previously been artificially infected with nematodes such as *Haemonchus contortus* and *Trichostrongylus colubriformis*. 1 to 3 animals are used per dose and per test respectively. Each sheep is treated with only a single dose.

An initial evaluation is carried out by comparing the number of worm eggs excreted in the faeces of the sheep before and after the treatment.

Seven to ten days after the treatment, the sheep are sacrificed and dissected. Evaluation is carried out by counting the worms remaining in the intestine after the treatment. Sheep which are infected but untreated at the same time and in the same manner are used as a control or comparison respectively.

In this test, a large reduction in the nematode attack is achieved using compounds of the formula I. Thus, for example, when using 20 mg of active substance per kg of body weight a reduction in the nematode attack of about 90% is effected with the following compounds: 1.1, 1.2, 1.3, 1.4, 2.1, 2.2, 2.3 and 2.4. This result is additionally also achieved in the case of individual compounds with a further reduced dose, for example with 10 mg of active substance per kg of body weight or still lower amounts of active substance.

3.2. Test on sheep infected with cestodes such as *Moniezia benedeni*

The active ingredient is administered in the form of a suspension using a stomach tube or by injection into the rumen of sheep which have previously been artificially infected with cestodes such as *Moniezia benedeni*. 3 animals are used per test and per dose respectively. Each sheep is treated with only a single dose. Seven to ten days after the treatment, the sheep are sacrificed and dissected. Evaluation is carried out by counting the worms remaining in the intestine after the treatment. Sheep infected but untreated at the same time and in the same manner are used as a control or comparison respectively. In this test, active ingredients from Table 1 or 2, for example the compounds nos. 1.1, 1.2, 1.3, 1.4, 2.1, 2.2, 2.3 or 2.4 effect an about 90% reduction of the cestode attack at doses of less than 20 mg/kg of body weight.

3.3. Test on sheep infected with *Fasciola hepatica*

The active ingredient is administered in the form of a suspension using a stomach tube or by injection into the rumen of sheep which have previously been artificially infected with *Fasciola hepatica*. 3 animals are used per test and per dose respectively. Each animal is treated with only a single dose.

An initial evaluation is carried out by comparing the number of worm eggs excreted in the faeces of the sheep before and after the treatment.

Three to four weeks after the treatment, the sheep are sacrificed and dissected. Evaluation is carried out by counting the liver flukes remaining in the bile ducts after the treatment. Sheep infected but untreated at the same time and in the same manner are used as a control or comparison respectively. The difference between the number of liver flukes found in the two groups gives the efficacy of the active ingredient tested.

In this test, active ingredients from Table 1 or 2 show a good action against *Fasciola hepatica* at doses of less than 20 mg of active substance/kg of body weight. Among these active ingredients, the compound no. 1.2 proves to be particularly active against *Fasciola hepatica*.

What is claimed is:

1. A compound of the general formula I

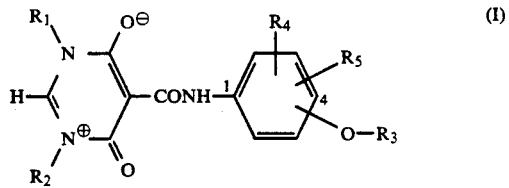

or in its hydrogenated form the formula (Ia)

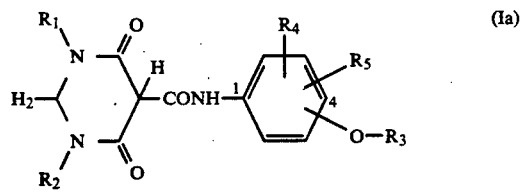

in which $R_1$ and $R_2$ independently of one another are $C_1$-$C_6$alkyl, allyl, $C_3$-$C_6$cycloalkyl, benzyl or phenyl; $R_3$ is unsubstituted or substituted pyridyl or quinolyl and $R_4$ and $R_5$ independently of one another are hydrogen, $C_1$-$C_4$alkyl, $C_1$-$C_4$alkoxy or halogeno-$C_1$-$C_3$alkyl, including its tautomeric forms and physiologically tolerable salts.

2. A compound of the formula I according to claim 1, in which $R_1$ and $R_2$ independently of one another are $C_1$-$C_6$alkyl, allyl, $C_3$-$C_6$cycloalkyl or phenyl and $R_3$, $R_4$ and $R_5$ have the meanings given in claim 1.

3. A compound of the formula I or Ia according to claim 2, in which $R_1$ and $R_2$ independently of one another are $C_1$-$C_4$alkyl, allyl or cyclopropyl; $R_3$ is a pyridyl or quinolyl radical which is unsubstituted or mono- to trisubstituted by substituents of the group consisting of $C_1$-$C_4$alkyl, methoxy, methylamino, dimethylamino, methylthio, trifluoromethyl, halogen and phenyl, $R_4$ is hydrogen or, $C_1$-$C_4$alkyl, or methoxy and $R_5$ is hydrogen or methyl.

4. A compound of the formula I or Ia according to claim 2, in which $R_1$ is $C_1$-$C_4$alkyl, allyl or $C_3$-$C_6$cycloalkyl, $R_2$ is $C_1$-$C_4$alkyl, $R_3$ is a pyridyl, or quinolyl radical which is unsubstituted or mono- to trisubstituted by substituents of the group consisting of $C_1$-$C_4$alkyl, halogeno-$C_1$-$C_4$alkyl, $C_1$-$C_4$alkoxy, halogeno-$C_1$-$C_4$alkoxy, $C_1$-$C_4$alkylthio, $C_1$-$C_3$alkylamino, di-($C_1$-$C_3$alkyl)amino, allyl, halogen, $C_3$-$C_6$cycloalkyl and phenyl and which is bonded via a carbon atom, $R_4$ is hydrogen, $C_1$-$C_4$alkyl or $C_1$-$C_4$alkoxy, and $R_5$ is hydrogen.

5. A compound of the formula I or Ia according to claim 4, in which $R_1$ is $C_1$-$C_2$alkyl, allyl or cyclopropyl, $R_2$ is $C_1$-$C_2$alkyl, $R_3$ is a pyridyl, quinolyl radical which is unsubstituted or mono- to trisubstituted by substituents from the group consisting of $C_1$-$C_4$alkyl, halogeno-$C_1$-$C_4$alkyl, $C_1$-$C_4$alkoxy, $C_1$-$C_4$alkylthio, di-($C_1$-$C_3$alkyl)amino, halogen or phenyl and which is bonded via a carbon atom, $R_4$ is hydrogen, $C_1$-$C_4$alkyl or $C_1$-$C_4$alkoxy, and $R_5$ is hydrogen or $C_1$-$C_4$alkyl.

6. A compound of the formula I or Ia according to claim 5, in which $R_1$ is $C_1$-$C_2$alkyl, allyl or cyclopropyl, $R_2$ is methyl, $R_3$ is a pyridyl, radical which is unsubstituted or mono- to trisubstituted by substituents of the group consisting of $C_1$-$C_4$alkyl, trifluoromethyl, methoxy, methylthio, chlorine or phenyl and which is bonded via a carbon atom, $R_4$ is hydrogen, $C_1$-$C_4$alkyl or $C_1$-$C_4$alkoxy and $R_5$ is hydrogen or $C_1$-$C_4$alkyl and the molecule moiety —$OR_3$ is in the meta- or para-position to the nitrogen atom of the carbamoyl group.

7. A compound of the formula I or Ia according to claim 6, in which $R_1$ is methyl or allyl, $R_2$ is methyl, $R_3$ is a pyridyl ring which is unsubstituted or mono- or disubstituted by substituents of the group consisting of $C_1$-$C_2$alkyl, halogeno-$C_1$-$C_2$alkyl, halogen or phenyl and which is bonded via a carbon atom, $R_4$ is hydrogen, $C_1$-$C_2$alkyl or $C_1$-$C_2$alkoxy, $R_5$ is hydrogen or methyl and the molecule moiety —$OR_3$ is in the meta- or para-position to the nitrogen atom of the carbamoyl group.

8. A compound of the formula I or Ia according to claim 7, in which $R_1$ is methyl, $R_2$ is methyl, $R_3$ is a pyridyl ring which is mono- or disubstituted by substituents of the group consisting of methyl, trifluoromethyl, chlorine and phenyl and which is bonded via a carbon atom, $R_4$ is hydrogen, methyl, isopropyl, methoxy or ethoxy, $R_5$ is hydrogen or methyl and the molecule moiety —$OR_3$ is in the meta- or para-position to the nitrogen atom of the carbamoyl group.

9. A compound of the formula I or Ia according to claim 8, in which $R_1$ is methyl, $R_2$ is methyl, $R_3$ is a pyridyl ring which is monosubstituted by trifluoromethyl or in total disubstituted by trifluoromethyl and another substituent of the group consisting methyl, trifluoromethyl, chlorine and phenyl and which is bonded via a carbon atom, $R_4$ is hydrogen, methyl, isopropyl or methoxy, $R_5$ is hydrogen or methyl and the molecule moiety —$OR_3$ is in the para-position to the nitrogen atom of the carbamoyl group.

10. A compound of the formula I according to claim 2, selected from the group consisting of:
1,3-dimethyl-5-[4-(4-trifluoromethyl-6-chloropyridyl-2-oxy)-phenylcarbamoyl]-4(6)-oxo-6(4)-oxido-(1H,5H)-pyrimidinium betaine;
1,3-dimethyl-3-[3-(3-chloro-5-trifluoromethylpyridyl-2-oxy)-4-chlorophenylcarbamoyl]-4-(6)-oxo-6(4)-oxido-(1H,5H)-pyrimidinium betaine;
1,3-dimethyl-5-[4-(4-trifluoromethylpyridyl-2-oxy)-phenylcarbamoyl]-4(6)-oxo-6(4)-oxido-(1H,5H)-pyrimidinium betaine;
1,3-dimethyl-5-[4-(3-chloro-5-trifluoromethylpyridyl-2-oxy)-phenylcarbamoyl]-4(6)-oxo-6(4)-oxido-(1H,5H)-pyrimidinium betaine.

11. A compound of the formula Ia according to claim 2, selected from the group consisting of:
1,3-dimethyl-5-[4-(4-trifluoromethyl-6-chloropyridyl-2-oxy)-phenylcarbamoyl]-4,6-(1H,3H,5H)-pyrimidinedione;
1,3-dimethyl-3-[3-(3-chloro-5-trifluoromethylpyridyl-2-oxy)-4-chlorophenylcarbamoyl]-4,6-(1H,3H,5H)-pyrimidinedione;
1,3-dimethyl-5-[4-(4-trifluoromethylpyridyl-2-oxy)-phenylcarbamoyl]-4,6-(1H,3H,5H)-pyrimidinedione;
1,3-dimethyl-5-[4-(3-chloro-5-trifluoromethylpyridyl-2-oxy)-phenylcarbamoyl]-4,6-(1H,3H,5H)-pyrimidinedione.

12. An anthelmintic composition, which contains, as an active component, at least one compound of the formula I or Ia, a tautomer or a salt thereof according to claim 1 in addition to carriers and other adjuncts.

13. A process for controlling parasitic helminths, wherein an anthelmintically active amount of a compound of the formula I or Ia according to claim 1 is administered to an animal.

14. 1,3-dimethyl-5-[4-(3-chloro-5-trifluoromethylpyridyl-2-oxy)-phenylcarbamoyl]-4(6)-oxo-6(4)-oxido-(1H,5H)-pyrimidinium betaine according to claim 10.

15. A compound of the formula I or Ia according to claim 3, in which $R_3$ is substituted by substituents of the group consisting of methyl, isopropyl, and tert-butyl.

16. A compound according to claim 3, wherein $R_3$ is substituted by chlorine.

17. A compound of the formula I or Ia according to claim 3, wherein $R_4$ is selected from the group consisting of methyl and isopropyl.

* * * * *